(12) United States Patent
Schaneville

(10) Patent No.: US 12,290,543 B1
(45) Date of Patent: *May 6, 2025

(54) BIOAVAILABLE COMPOSITIONS COMPRISING CANNABINOIDS AND CYCLODEXTRINS

(71) Applicant: Scott Schaneville, Los Angeles, CA (US)

(72) Inventor: Scott Schaneville, Los Angeles, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/091,389

(22) Filed: Nov. 6, 2020

Related U.S. Application Data

(63) Continuation-in-part of application No. 16/387,867, filed on Apr. 18, 2019, now Pat. No. 10,632,164, which is a continuation of application No. 15/485,655, filed on Apr. 12, 2017, now Pat. No. 10,265,362.

(60) Provisional application No. 62/338,762, filed on May 19, 2016, provisional application No. 62/321,480, filed on Apr. 12, 2016.

(51) Int. Cl.
| | |
|---|---|
| *A61K 36/185* | (2006.01) |
| *A61K 9/00* | (2006.01) |
| *A61K 9/06* | (2006.01) |
| *A61K 31/352* | (2006.01) |
| *A61K 47/10* | (2017.01) |
| *A61K 47/26* | (2006.01) |
| *A61K 47/36* | (2006.01) |

(52) U.S. Cl.
CPC ............ *A61K 36/185* (2013.01); *A61K 9/006* (2013.01); *A61K 9/06* (2013.01); *A61K 31/352* (2013.01); *A61K 47/10* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | |
|---|---|---|
| 6,596,298 B2 | 7/2003 | Leung et al. |
| 2016/0051510 A1 | 2/2016 | Allen et al. |

FOREIGN PATENT DOCUMENTS

FR 2906141 * 3/2008

OTHER PUBLICATIONS

Canadian Intellectual Property Office, Canadian Office Action issued in Canadian Application No. 3020798, dated May 3, 2023 (4 pages).

* cited by examiner

*Primary Examiner* — Michael V Meller
(74) *Attorney, Agent, or Firm* — KEATY LAW FIRM LLC; Thomas S. Keaty

(57) ABSTRACT

Bioavailable compositions are provided. The bioavailable compositions comprise emulsions. The emulsions comprise: water; a cannabinoid; a carrier; an emulsifier; and a cyclodextrin. The bioavailable compositions may further comprise an excipient and/or a terpene. The bioavailable compositions may comprise thin films. The thin films may be mucosally dissolvable films.

2 Claims, No Drawings

BIOAVAILABLE COMPOSITIONS COMPRISING CANNABINOIDS AND CYCLODEXTRINS

RELATED U.S. APPLICATION DATA

This application claims priority to U.S. Provisional Patent Application No. 62/931,4601, filed on Nov. 6, 2019. This application also claims priority to and is a continuation-in-part of U.S. patent application Ser. No. 16/849,921, filed on Apr. 15, 2020, which claims priority to and is a continuation of U.S. patent application Ser. No. 16/387,867, filed on Apr. 18, 2019, and now issued as U.S. Pat. No. 10,632,164, which claims priority to and is a continuation of U.S. patent application Ser. No. 15/485,655, filed on Apr. 12, 2017, and now issued as U.S. Pat. No. 10,265,362, which claims the benefit of priority to U.S. Provisional Patent Application No. 62/321,480, filed on Apr. 12, 2016, and U.S. Provisional Application Patent Application No. 62/338,762, filed on May 19, 2016. The entire contents of each of these applications are incorporated herein by reference.

FIELD

The present disclosure relates to bioavailable compositions comprising a cannabinoid and a cyclodextrin.

BACKGROUND

Cannabinoids have a long history of medicinal and recreational use. Cannabinoids are generally administered into the body by inhalation of smoke or vapors, ingestion of edible capsules or liquid extracts such as tinctures or oils, topical solutions, ingestible films, and ingestible wafers. Each mode of delivery has its own challenges.

One set of challenges is maximizing bioavailability and onset time, while minimizing unintended health risks. Bioavailability, a subcategory of absorption, is the fraction of an administered dose of unchanged drug that reaches the systemic circulation and is one factor that may influence a consumer's choice of means of administration. Onset time is the duration of time it takes for a drug's effects to come to prominence upon administration. Thus, in the context of cannabinoids, onset time is the amount of time it takes for the cannabinoids to begin showing psychological and physiological signs in the subject. Bioavailability may influence onset time; i.e., a more bioavailable cannabinoid composition may have a faster onset time.

Sublingual administration involves placing a drug under the tongue to dissolve and absorb into the blood through the mucosal tissue there. Buccal administration involves placing a drug between the gums and cheek, where it dissolves and is absorbed into the blood through the mucosal tissue there. Cannabinoids available in *cannabis* extracts may be hydrophobic, and may not mix well with aqueous solutions, thus reducing their bioavailability via buccal and sublingual mucosa.

Some cyclodextrins with hydrophobic molecules may be able to penetrate body tissues and may release biologically active compounds. Cyclodextrins may enhance mucosal penetration of drugs. What is needed are compositions comprising cannabinoids and cyclodextrins, wherein the cannabinoids have a relatively high bioavailability, including but not limited to sublingually and buccally.

SUMMARY

In one aspect, a composition is provided, wherein the composition comprises an emulsion. The emulsion comprises: water; a cannabinoid; a carrier; an emulsifier; and a cyclodrextrin. In one aspect, the emulsion further comprises an excipient. In one aspect, the emulsion further comprises a terpene.

In one aspect, a composition is provided, the composition comprising: water; a cannabinoid; a medium chain triglyceride (an MCT); one or more of polysorbate 80, span 80, polyoxyl 40 hydrogenated castor oil, macrogolglycerol hydroxystearate, polyglycerate 60, glycerine, and sorbitan stearate; and a β-cyclodextrin. In one aspect, the β-cyclodextrin comprises hydroxypropyl-β-cyclodextrin (HBC). In one aspect, the composition further comprises one or more of hydroxypropyl methyl cellulose (HPMC), hydroxypropyl cellulose (HPC), and methyl cellulose. In one aspect, the composition further comprises a terpene.

In one aspect, a composition is provided, the composition comprising: water; a cannabinoid; an MCT; polysorbate 80, span 80; HBC; and HPMC. In one aspect, the composition further comprises a terpene.

DETAILED DESCRIPTION

In one aspect, a composition is provided, wherein the composition comprises an emulsion. The emulsion comprises: water; a cannabinoid; a carrier; an emulsifier; and a cyclodextrin. In one aspect, the emulsion further comprises an excipient. In one aspect, the composition further comprises a terpene.

Cannabinoids

The term cannabinoid, as used in this disclosure, may include any of a group of closely related compounds that include cannabinol and the active constituents of *cannabis*. For example, cannabinoids may include: cannabichromenes (cannabichromene (CBC), cannabichromenic acid (CBCA), cannabichromevarin (CBCV), and cannabichromevarinic acid (CBCVA)); cannabicyclols (cannabicyclol (CBL), cannabicyclolic acid (CBLA), and cannabicyclovarin (CBLV)); cannabidiols (cannabidiol (CBD), cannabidiol monomethylether (CBDM), cannabidiolic acid (CBDA), cannabidiorcol (CBD-C1), cannabidivarin (CBDV), and cannabidivarinic acid (CBDVA)); cannabielsoins (cannabielsoic acid B (CBEA-B), cannabielsoin (CBE), and cannabielsoin acid A (CBEA-A)); cannabigerols (cannabigerol (CBG), cannabigerol monomethylether (CBGM), cannabigerolic acid (CBGA), cannabigerolic acid monomethylether (CBGAM), cannabigerovarin (CBGV), and cannabigerovarinic acid (CBGVA)); cannabinols and cannabinodiols (cannabinodiol (CBND), cannabinodivarin (CBVD), cannabinol (CBN), cannabinol methylether (CBNM), cannabinol-C2 (CBN-C2), cannabinol-C4 (CBN-C4), cannabinolic acid (CBNA), cannabiorcool (CBN-C1), and cannabivarin (CBV)); cannabitriols (10-ethoxy-9-hydroxy-delta-6a-tetrahydrocannabinol, 8,9-dihydroxy-delta-6a-tetrahydrocannabinol, cannabitriol (CBT) and cannabitriolvarin (CBTV)); delta-8-tetrahydrocannabinols (delta-8-tetrahydrocannabinol (48-THC) and delta-8-tetrahydrocannabinolic acid (48-THCA)); delta-9-tetrahydrocannabinols (delta-9-tetrahydrocannabinol (THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THC-V), and delta-9-tetrahydrocannabivarinic acid (THC-VA), delta-9-cis-tetrahydrocannabinol (cis-THC), and trihydroxy-delta-9-tetrahydrocannabinol (triOH-THC)), and various other miscellaneous cannabinoids, e.g., 10-oxo-delta-6a- tetrahydrocannabinol (OTHC), cannabichromanon (CBCF), cannabifuran (CBF), cannabiglendol, cannabiripsol (CBR), cannbicitran (CBT), dehydrocannabifuran (DCBF), and 3,4,5,6-tetrahydro-7-hydroxy-alpha-alpha-2-trimethyl-9-n-propyl-2,6-methano-2H-1-benzoxocin-5-methanol (OH-iso-HHCV), and mixtures thereof. In certain aspects, the cannabinoid comprises THC, THC-V, CBD, CBG, and/or CBN.

Carriers

Bioavailability is the biggest concern when determining the best carrier. Bioavailability is largely determined by the types of fat molecules contained in the carrier oil. In one aspect, the carrier may be an MCT. MCTs are triglycerides with two or three fatty acids having an aliphatic tail of 6-12 carbon atoms, i.e., medium-chain fatty acids. MCTs may include, for example, caproic acid, caprylic acid, capric acid, and lauric acid.

In one aspect, the carrier may be coconut oil, including fractionated coconut oil. Coconut oil is comprised of an abundance of saturated fats, particularly MCTs. Fractionated coconut oil is coconut oil that has had the longer fat molecules removed to isolate the MCTs. In other aspects, the carrier may be palm oil, olive oil, avocado oil, hemp seed oil, grape seed oil, glycerol/glycerin, propylene glycol, fatty acids, oleic acid, linoleic acid, vegetable oil, vegetable shortening, soybean oil, sunflower oil, peanut oil, corn oil, canola oil, rice bran oil, lard, suet, and butter. Long chain triglycerides may also be suitable carriers. A suitable carrier may include a mixture of any of these examples.

Unless otherwise specified, recitation of "MCTs" includes isolated MCTs (e.g., caproic acid, caprylic acid, capric acid, and lauric acid, and mixtures thereof) produced by fractionation or extraction from MCT-containing substances (such as coconut oil or palm oil), as well as MCT-containing substances.

Emulsifiers

Emulsifiers include any compound that stabilizes an emulsion. Suitable emulsifiers include polysorbate 80, span 80, polyoxyl 40 hydrogenated castor oil, macrogolglycerol hydroxystearate, polyglycerate 60, glycerine, sorbitan stearate, polysorbate 20, polysorbate 40, polyoxyethylene (20) sorbitan monostearate, sorbitan monooleate, sorbitan oleate, polyethylene glycol, monoglycerides, diglycerides, triglycerides, phospholipids, lecithin, sodium bis(2-ethylhexyl) sulfosuccinate (AOT), sodium mono- and dimethylnaphthalene sulfonate (SMDNS), lecithin, sunflower lecithin, quillaja extract, and combinations thereof. In one aspect, the emulsifier comprises a combination of polysorbate 80 and span 80. In a more specific aspect, the emulsifier comprises a combination of polysorbate 80 and span 80 in a relative weight ratio of about 4: about 1 (although weight ratios of about 1: about 1, about 2: about 1, about 3: about 1, about 5: about 1, and so forth, are contemplated).

Cyclodextrins

Cyclodextrins are cyclic oligosaccharides consisting of 6, 7, or 8 glucopyranose units, usually referred to as α-, β-, or γ-cyclodextrins, respectively. These compounds have rigid doughnut-shaped structures, with an electron-rich, hydrophobic interior, making them natural complexing agents. Cavity size is the major determinant as to which cyclodextrin is used in complexation. The cavity diameter of β-cyclodextrins is well-suited for use with molecules of relatively significant size. For this reason, β-cyclodextrins are most commonly used as complexing agents.

Suitable β-cyclodextrins include, for example, the following

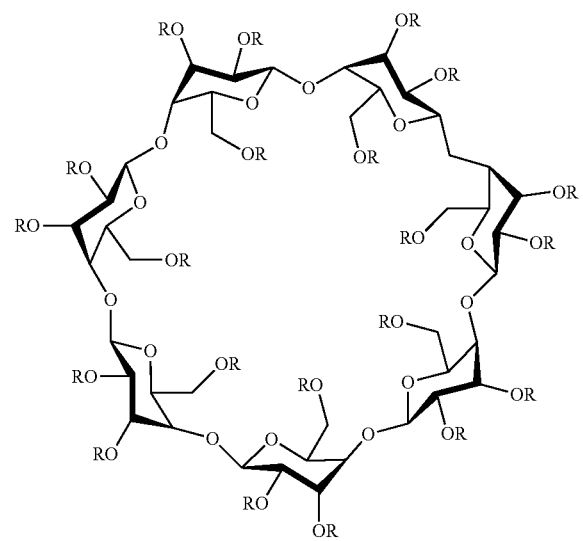

wherein R=—H (β-cyclodextrin), —$CH_2CHOHCH_3$ (2-hydroxyproply-β-cyclodextrin or HBC), —$(CH_2)_4$$SO_3Na^+$ (sulfobutylether β-cyclodextrin sodium salt), —$CH_3$ (randomly methylated β-cyclodextrin), branched β-cyclodextrin (glucosyl or maltosyl group), and mixtures thereof.

Excipients

As used herein, an excipient is a substance formulated alongside the cannabinoid, included for the purpose of long-term stabilization or to confer a therapeutic enhancement on the cannabinoid in the final dosage form, such as facilitating drug absorption, reducing viscosity, or enhancing solubility. Suitable excipients include saccharide-based polymers that are water soluble. For example, the saccharide-based polymer may be cellulose or a cellulose derivative. Specific examples of useful saccharide-based, water soluble polymers include, but are not limited to, polydextrose, pullulan, HPMC, HPC, hydroxypropyl cellulose, carboxymethyl cellulose, sodium aginate, xanthan gum, tragancanth gum, guar gum, acacia gum, arabic gum, starch, gelatin, and combinations thereof. The saccharide-based polymer may be at least one cellulosic polymer, polydextrose, or combinations thereof.

Suitable non-saccharide based, water soluble polymers include polyethylene oxide, polyvinylpyrrolidone, polyvinyl polyethylene alcohol, glycol, polyacrylic acid, methylmethacrylate copolymer, carboxyvinyl copolymers, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate, and combinations thereof.

The polymer may also be a combination of substances, such as HPMC and polyethylene oxide; polydextrose and polyethylene oxide; or polydextrose, HPMC, and polyethylene oxide.

In one aspect, the composition comprises: water; a cannabinoid; one or more of MCTs, coconut oil, palm oil, and a combination thereof; one or more of polysorbate 80, span 80, polyoxyl 40 hydrogenated castor oil, macrogolglycerol hydroxystearate, polyglycerate 60, glycerine, and sorbitan stearate; and a cyclodextrin. In one aspect, the cyclodextrin comprises a β-cyclodextrin. In one aspect, the β-cyclodextrin comprises HBC. In one aspect, the composition further comprises an excipient. In one aspect, the excipient comprises one or more of HPMC, HPC, and methyl cellulose.

In one aspect, the composition comprises: water; a cannabinoid; coconut oil; polysorbate 80 and span 80; HBC; and HPMC. In one aspect, the composition further comprises a terpene.

Administration Media

In one aspect, the composition may be administered via a dissolvable film. In one example, the film may be a non-toxic sublingual or orally dissolving film or mucosally dissolving film. A "mucosally dissolvable film" refers to any thin film that allows an active agent to seep or absorb through the mucosal membrane of any mammalian subject, as distinguished from an oral film that is swallowed such that the film components, including the active agent, traverse the digestive tract of the subject.

Other aspects include any administration method where increased absorptivity and/or bioavailability would be advantageous, such as, for example, ingestible capsules or liquid extracts such as tinctures or oils, beverage emulsions, topical solutions, ingestible films, and ingestible wafers.

In more specific aspects, the cannabinoid comprises THC, THC-V, CBD, CBG, CBC, and/or CBN, and the administration medium is a thin film. In even more specific aspects, the cannabinoid comprises THC, THC-V, CBD, CBG, CBC, and/or CBN, the administration medium is a thin film, and the cannabinoid is the main constituent of the film. In such an aspect, the cannabinoid may be in a purified form such that the concentration of the THC, THC-V, CBD, CBG, CBC, and/or CBN is greater than 90%, greater than 95%, greater than 98%, or greater than or about 99%. The purified substances, if used in the preparation of the film, may also be purchased from manufacturers. For example, the commercially available Elixinol 99.4% hemp extract isolate, EX-513W, contains 90-100% CBD and no THC and may be suitable for the preparation of a suitable film. Similarly, an extract containing more than 90% of THC and little or no CBD may be purchased from CLEAR. In one example, a film formulation may comprise at least 90% and up to about 100% CBD and may be present in the film from about 1% to about 70% by weight of the film. In certain aspects, cannabinoids may also be used in a less purified form such that the concentration of, e.g., CBD or THC, is less than about 90%, about 70%, about 60%, about 50%, about 30%, or about 15%.

The cannabinoid may be prepared into an emulsion that if formed into a film, such as an orally dissolving film, the cannabinoid may be present from less than 1% to greater than 60% by weight of the film.

In several aspects, commercially available CBD oil such as ELIXINOL 35% CBD Hemp Oil, EX-AMBR-21 (raw and decarbed) which contains 31-5% to 38.5% CBD and 1.05% to 1.2% THC or ELIXINOL 4% CBD Hemp Oil, EX-213 (raw and decarbed) containing 3.6% to 4.4% CBD and 0% THC or ELIXINOL 17.4% CBD Hemp Oil, EX-913 (raw and decarbed) containing 15.7% to 19.1% CBD and only a trace amount of THC (0.51%) may be used in the preparation of the films.

Other Components

In addition to the cannabinoids, carriers, emulsifiers, cyclodextrins, and excipients, the films may comprise permeability or penetration enhancers or absorption enhancers to improve the absorption of the cannabinoid by the mucosal tissues of a subject, taste-masking agents or bitter blockers to mask the bitter taste of the cannabinoid, and thickening agents to improve the viscosity of the films or emulsions. The penetration enhancers, if present in the film, may include compounds such as, but not limited to, calcium chelators such as EOTA, polycarboxylic acids, zonula occluding toxin, poly-L-arginine, chitosan derivatives, niacin, omega 3 or 6 fatty acids or other fatty acids, menthol, sodium caprate, sodium deoxycholate, dipotassium glycyrrhizinate, 25 furanocoumarins and grapefruit derivatives, bile salts, ethylenediaminetetraacetic acid, tocopheryl polyethyleneglycol succinate (TPGS), derivatives thereof, and combinations thereof, or the like. Permeability enhancers may include dimethyl isosorbide (DMI) and/or dimethyl sulfoxide (DMSO), with or without propylene glycol (PG). These penetration or absorption enhancers may be present in an amount ranging from 0.001% to about 10% by weight of the film. In one aspect, the amount of penetration enhancer in the film may range from about 0.1% to about 3% by weight of the film.

The taste-masking agent on the other hand, if present in the film, may be selected from kleptose, cyclodextrins, hydroxypropyl-beta-cyclodextrin, ginger, anise, cinnamon, peppermint, licorice, fruit flavoring, citric acid, fruit juice, sweeteners, sucrose, glucose, fructose, mannitol, saccharin, aspartame, sucralose, monk fruit, agave syrup, agave nectar, maple syrup, erythritol, xylitol, yacon syrup, neotame, *Stevia* plant, *Stevia* plant derivatives, honey, derivatives thereof, and combinations thereof. The amount of the taste-masking agents or bitter blockers in the film may range from about 0.001 to 5% by weight of the film, including from 0.001 to 0.5% by weight of the film.

The thickening agents, if present, may be selected from acetylated distarch adipate, agar, alginic acid, arrowroot, beta-glucan, calcium alginate, sodium alginate, carrageenan, *cassia* gum, chondrin, collagen, corn starch, dextrin, disodium phosphate, disodium pyrophosphate, 25 filé powder, galactomannan, gelatin, gellan gum, glucomannan, guar gum, gulaman, gum karaya, hydroxypropyl distarch phosphate, hydroxypropyl methylcellulose, hypromellose, irvingia *gabonensis*, konja, kudzu, locust, bean gum, maltodextrin, methyl cellulose, millet jelly, modified starch, monodora pyristica, monosodium phosphate, mung bean, natural gum, njangsa, pullulan, pectin, phosphate distarch, phosphate, polydextrose, potassium 30 bitartrate, potato starch, *psyllium* seed husks, sago, salep, flour, sodium phosphate, starch, tapioca, tapioca starch, tetrasodium pyrophosphate, tragacanth, trisodium, phosphate, waxy corn, and xanthan gum.

The film may further include one or more components in a film-forming matrix such as, for example, a film-forming agent; a filler; a plasticizer; a taste-masking agent; a coloring agent; additional solubilizing agents; an effervescent agent; an antioxidant; an absorption enhancer; a disintegrating agent; a pH modifying or buffer agent; a surfactant; additional complexing agents; a bio-adhesive agent; a sheet adhesive; an identifying agent; an anti-counterfeiting agent; a tracking agent; a transporter inhibitor agent; a transporter inducer agent; additional emulsifying agents and self-emulsifying system agents; a crystallization inhibitor; a crystallization promoter; a super-saturation promoting agent; an antimicrobial preservative; a catalyst; a chelating agent; particles; an organoleptic agent; a flavoring agent; a scent agent; an identifying device; and/or an anti-counterfeiting device. These types of ingredients can be exemplified by substances that are commonly used for pharmaceutical compositions or other ingestible compositions. Preferably, these types of ingredients are defined as generally recognized as being safe (GRAS) by a government agency, such as the U.S. FDA. In one aspect, the ingredients may be defined as being approved by a select committee on GRAS substances (SCOGS), such as which can be found at the U.S. FDA website, which is incorporated herein by specific reference in its entirety.

The film of the present disclosure may also be prepared from agents selected from methylcellulose, HPMC, ethylcellulose, sodium alginate, poly(methacrylic acid-co-ethyl acrylate), poly(methacrylic acid-co-methyl methacrylate), starch, 30 polyvinylpyrrolidone, polylactic acid (PLA), poly-L-lactide (PLLA), poly-D-lactide (PLDA), poly(lactic-co-glycolic acid) (PLGA), chitosan, chitin, pullulan, derivatives thereof, and combinations thereof. The plasticizer when used in the preparation of the film may be selected from glycerine, triacetin, triacetyl citrate, polyethyleneglycol, mineral oil, myglyol, derivatives thereof, and combinations thereof.

The film compositions may further include food colorants, such as carotenoid compounds and FD&C red, green, yellow, and blue, or the like. The solubilizing agent can be selected from polyvynilpyrrolidone, polyvinylcaprolactam-polyvinylacetate-polyethyleneglycol copolymer, fatty acids, castor oil, cyclodextrins, polyethyleneglycol, glyceryl distearate, lecithin, monoglycerides, diglycerides, triglycerides, propylene glycol monostearate, labrafils (e.g., oleoyl macrogol-6 glycerides, oleoyl polyoxyl-6-glycerides, linoleoyl macrogol-6 glycerides, linoleoyl polyoxyl-6 glycerides, lauroyl macrogol-6 glycerides, lauroyl polyoxyl-6 glycerides), labrasols (e.g., caprylocaproyl macrogol-8 glycerides, caprylocaproyl polyoxyl-8 glycerides), solutols (e.g., polyoxyethylene esters of 12-hydroxystearic acid), soluplus (e.g., polyvinyl caprolactam-polyvinyl acetate-polyethylene glycol graft co-polymer), derivatives thereof, and combinations thereof. Soluplus can also be used as a film-forming agent.

The effervescent agent, if present in the film, may be selected from sodium carbonate, bicarbonate, potassium carbonate, calcium carbonate, citric acid, malic acid, tartaric acid, adipic acid, fumaric acid, derivatives thereof, and combinations thereof.

The antioxidant, if present in the film, may be selected from tocopherol, vitamin E, resveratrol, ascorbyl palmitate, tert-butylhydroquinone, resveratrol, nordihydroguaiaretic acid, cysteine, propyl gallate, octyl gallate, 3-tert-butyl-4-hydroxyanisole, butylated hydroxytoluene, ascorbic acid, derivatives thereof, and combinations thereof, or the like.

The disintegrating agent, if present in the film, may be selected from croscarmellose sodium, sodium starch glycolate, insoluble polyvinylpyrrolidone, carboxymethylcellulose, derivatives thereof, and combinations thereof, or the like.

The film may also include a pH modifier or buffer agent selected from sodium carbonate, magnesium carbonate, calcium carbonate, sodium hydroxide, potassium hydroxide, ascorbic acid, citric acid, succinic acid, fumaric acid, derivatives thereof, and combinations thereof.

The surfactant, if present in the film, may be selected from sodium lauryl sulfate, poloxamers, sorbitan esters, polysorbates, sorbitans, stearic acid, derivatives thereof, and combinations thereof.

Additional complexing agents, if present in the film, may be selected from calcium glycerophosphate, dodecyl 2-(N, N-dimethylamino) propionate, zinc, dextran, pectin, copper acetate, sodium deoxycholate, calcium, magnesium, derivatives thereof, and combinations thereof.

The bio-adhesive agent, if present in the film, may be selected from gelatin, starch, glycoproteins, proteins, carbohydrates, mucopolysaccharides, derivatives thereof, and combinations thereof.

The sheet adhesive, if present in the film, may be selected from polyvinylpyrrolidone, polyvinyl alcohol, polyvinyl acetate, confectionary glue, starch, derivatives thereof, or combinations thereof.

The tracking agent, identifying agent, or anti-counterfeiting agent, if present in the film, may be selected from fluorescein, rhodamine, succinimidyl esters, maleimide activated fluorophores, fluorescent dyes, fluorescent particles, infrared active particles, near infrared active particles, metallic nanoparticles, polymeric particles, silica based nanoparticles, SERS (Surface Enhanced Raman Spectroscopy) particles, raman active particles, derivatives thereof, and combinations thereof.

The osmotic agent, if present in the film, may be selected from mannitol, osmitrol, dextrose, sucrose, fructose, sodium chloride, potassium chloride, xylitol, sorbitol, lactose, potassium phosphate, derivatives thereof, or combinations thereof.

The transporter inhibitor, if present in the film, may be selected from elacridar, zosuquidar, glibenclamide, quinaxoline derivatives, phenylalanine, arginyl naphthylamide, grapefruit derivatives, furanocoumarins, derivatives thereof, and combinations thereof. The transporter inducer, if present in the film, may be selected from xenobiotics, diallyl sulfide, dexamethasone, derivatives thereof, and combinations thereof.

Additional emulsifying agents, if present in the film, may be selected from tocopheryl polyethyleneglycol succinate (TPGS), Cremophor (e.g., non-ionic polyethoxylated detergents), Lutrol (e.g., polyethylene glycol), Poloxamers (e.g., polyethylene-polypropylene glycol), cholesterol, octyldodecanol, polyoxylglycerides, derivatives thereof, and combinations thereof.

The self-emulsifying system, if present in the film, may be selected from Labrasol, Labrafil, Cremophor, Pluronics, Lutrol, poloxamers, polysorbates, ethyl linoleate, mono- and diglycerides of capric and caprylic acids, tocopherol acetate, Solutol, soybean oil, tocopheryl polyethyleneglycol succinate (TPGS), Capmuls, derivatives thereof, and combinations thereof, or the like.

Crystallization inhibitors, if present in the film, may be selected from polyvinylpyrollidone, hydroxypropyl methylcellulose, silicon dioxide, dextrins, dextrans, bile acids, sterols, polysebacic anhydride, derivatives thereof, and combinations thereof.

The supersaturating promoting agent, if present in the film, may be selected from hydroxyproyl methylcellulose, hydroxypropylmethyl cellulose acetate succinate, polyvinylpyrollidone, derivatives thereof, and combinations thereof.

The antimicrobial preservative, if present in the film, may be selected from benzoic acid, sodium benzoate, methyl paraben, propyl baraben, butyl paraben, sorbic acid, propionic acid, dehydroacetic acid, derivatives thereof, and combinations thereof.

The catalyst, if present in the film, may be selected be heavy metals selected from Ni, Cr, Mn, Zn, Fe, or combinations thereof, or the like.

An organoleptic agent, if present in the film, may be a flavorant or scent, such as selected from vanilla, bubble gum, fruit flavor, mint, chocolate, licorice, marshmallow, peanut butter, aspartame, sucralose, sucrose, glucose, citric acid, *stevia* plant, derivatives thereof, or combinations thereof. The organoleptic agent for a veterinary aspect may be selected from glutamates, chicken flavor, umami flavoring, beef flavor, fish flavor, bacon flavor, or the like.

The chelating agent, if present in the film, may be selected from disodium edetate, EDTA, pentetic acid, derivatives thereof and combinations thereof.

Starches such as corn starch, potato starch, pregelatinized and modified starches thereof, cellulosic agents such as Act-di-sol, montmorrilonite clays including cross-linked PVP, sweeteners, bentonite and VEEGUM™, microcrystalline cellulose, alginates, sodium starch glycolate, gums such as agar, guar, locust bean, karaya, pectin, and tragacanth may also be included in the film.

Disintegrants, if present in the film, may comprise up to about 20 weight percent and preferably between about 2 and about 5 percent of the total weight of the composition.

The film may also include surfactants such as sodium lauryl sulfate, sodium dodecyl sulfate and tween; bile salts such as sodium taurocholate; fatty acids such as oleic and linoleic acid; and non-surfactants such as AZONE and dialkyl sulfoxides.

Coloring agents may also be present in the film and could include titanium dioxide, and dyes suitable for food such as those known as F.D. & C. dyes and natural coloring agents such as grape skin extract, beet red powder, beta-carotene, annato, carmine, turmeric, paprika, etc. The coloring agent, if present in the film, may range from about 0 to about 2.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, *eucalyptus*, thyme oil, cedar leave oil, oil of nutmeg, oil of sage, oil of bitter almonds and *cassia* oil. Also useful as flavors are vanilla, citrus oil, including lemon, orange, grape, lime and grapefruit, and fruit essences, including apple, pear, peach, strawberry, raspberry, cherry, plum, pineapple, apricot, blueberry, mango, blackberry, coconut, cranberry, tarragon, and so forth. Flavors which have been found to be particularly useful include commercially available orange, tangerine, grape, cherry, and bubble gum flavors, and mixtures thereof. The amount of flavoring may depend on a number of factors, including the organoleptic effect desired. Flavors may be present in an amount ranging from about 0.5 to about 3.0 by weight based upon the weight of the composition.

Vitamins, if present in the film, refer to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), nicotinamide adenine dinucleotide (AND), nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes. A mineral may be used in the films, and refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The film may also include a dietary supplement, which is a substance which has an appreciable nutritional effect when administered in small amounts. Dietary supplements include, without limitation, such ingredients as bee pollen, bran, wheat germ, kelp, cod liver oil, *ginseng*, and fish oils, amino-acids, proteins and mixtures thereof. Dietary supplements may also include, without limitation, appetite suppressants, sleeping aids, such as melatonin, botanical dietary supplements, caffeine, and erectile dysfunction supplements. As will be appreciated, dietary supplements may incorporate vitamins and minerals.

The film or emulsion may also include terpenes. Terpenes include, without limitation, such compounds as pinene terpene, linalool terpene, caryophyllene terpene, humulene terpene, myrcene terpene, limonene terpene, alpha bisabolol, alpha phellandrene, alpha pinene, beta caryophyllene, beta pinene, cadinene, camphene, camphor, citral, citronellol, delta-3-carene, eucalyptol, eugenol, gamma terpinene, geraniol, limonene, myrcene, nerol, nerolidol, ocimene, para-cymene, phytol, pulegone, terpineol, terpinolene, valencene, and a mixture thereof.

The film may further include binders such as but not limited to acacia, tragacanth, gelatin, starch, cellulose materials such as methyl cellulose and sodium carboxymethyl cellulose, alginic acids and salts thereof, polyethylene glycol, guar gum, polysaccharide, sugars, invert sugars, poloxomers (PLURONIC F68, PLURONIC F127), collagen, albumin, gelatin, cellulosics in nonaqueous solvents, and combinations of the above and the like. Other binders may include, for example, polypropylene glycol, polyoxyethylene-polypropylene copolymer, polyethylene ester, polyethylene sorbitan ester, polyethylene oxide or combinations thereof and the like. Hydrophobic binders can also be used in the invention.

EXAMPLES

Tables 1-5 show example experimental data illustrating that the water solubility of cannabinoids is substantially improved when the cannabinoids are used in combination with a cyclodextrin and, optionally, a cellulosic excipient.

General Experimental Procedure: Emulsions including water, cannabinoid oil, MCTs, and polysorbate 80 and span 80 were combined with HBC and, in some experiments, HPMC, at different concentrations. The samples were sonicated. After sonication, the samples were filtered through a 0.45 µm filter (i.e., filter pore size 0.45 µm) that mimics the pore size of the sublingual tissue in the mouth. The cannabinoid content in the filtered samples was measured after the filtration. Four samples were prepared and tested for each HBC/HPMC concentration. The experimental results shown in Tables 1-5 are averaged results of the four tests. The measured cannabinoid content may be correlated to the bioavailability of the cannabinoid through the sublingual delivery mode. The higher the cannabinoid content in the filtered emulsion, the higher the bioavailability, and the more cannabinoid can be rapidly absorbed into the bloodstream, bypassing the gastrointestinal and liver routes.

Example 1—THC

TABLE 1

| | | | THC | | |
|---|---|---|---|---|---|
| | THC | HBC | | THC content after filtration | |
| Sample No. | content (mg/ml) | (g/ 100 ml) | HPMC (g/100) | (mg/ml) | (%) | Enhancement (%) |
| 1 | 50.00 | 0.0 | 0.0 | 1.54 | 3.08 | 0 |
| 2 | 50.00 | 1.0 | 0.0 | 4.78 | 9.56 | 210 |
| 3 | 50.00 | 2.5 | 0.0 | 5.75 | 11.50 | 273 |
| 4 | 50.00 | 5.0 | 0.0 | 6.95 | 13.90 | 351 |
| 5 | 50.00 | 7.5 | 0.0 | 8.92 | 17.84 | 479 |
| 6 | 50.00 | 10.0 | 0.0 | 11.75 | 23.50 | 663 |
| 7 | 50.00 | 12.5 | 0.0 | 13.10 | 26.20 | 751 |
| 8 | 50.00 | 15.0 | 0.0 | 14.84 | 29.68 | 864 |
| 9 | 50.00 | 17.5 | 0.0 | 16.90 | 33.80 | 997 |
| 10 | 50.00 | 20.0 | 0.0 | 19.10 | 38.20 | 1140 |
| 11 | 50.00 | 22.5 | 0.0 | 21.94 | 43.88 | 1325 |
| 12 | 50.00 | 25.0 | 0.0 | 24.50 | 49.00 | 1491 |
| 13 | 50.00 | 12.5 | 0.25 | 18.15 | 36.30 | 1079 |
| 14 | 50.00 | 12.5 | 0.50 | 23.10 | 46.20 | 1400 |
| 15 | 50.00 | 12.5 | 1.00 | 24.35 | 48.70 | 1481 |
| 16 | 50.00 | 12.5 | 1.25 | 26.02 | 52.04 | 1590 |

With reference to Table 1, Sample No. 1 is the reference sample, which is an emulsion of water and one milliliter of THC oil at a concentration of 50 milligrams (mg) of THC per milliliter of THC oil (e.g., 50 mg/ml). Sample Nos. 2-16 are emulsions of water, 50 mg/ml THC, a carrier (MCT), an emulsifier (polysorbate 80 and span 80), and a water solubility enhancing agent (HBC). Emulsions of Samples 13-16 further include HPMC, which may further enhance the water solubility of the THC. The MCT, polysorbate 80 and span 80 are present in amounts appropriate to form a water emulsion. The amounts of HBC and HPMC present are characterized in terms of grams per 100 milliliter (g/100 ml) of the emulsion. Sample Nos. 1-16 were sonicated before filtration through a 0.45 μm filter.

With reference to Sample No. 1, after filtration, only about 1.54 mg/ml of THC is measured in the filtered emulsion. This indicates that only about 3.08% of THC passed through the 0.45 μm filter (e.g., 1.54 mg/50 mg×100%=3.08%). With reference to Sample No. 2, with the addition of HBC at a concentration of 1 g/100 ml, the carrier (MCT), and the emulsifier (polysorbate 80 and span 80), about 4.78 mg/ml of THC is measured in the filtered emulsion. About 9.56% of THC passed through the 0.45 μm filter (e.g., 4.78 mg/50 mg×100%=9.56%). This indicates that at the HBC concentration of 1 g/100 ml, the water solubility of THC is enhanced by about 210% (e.g., (4.78 mg-1.54 mg)/1.54 mg×100%=210%). There is more THC dissolved in Sample No. 2 than in Sample No. 1, leading to more THC passed through the filter that mimics the sublingual tissue in the mouth. As a result, THC in Sample No. 2 would presumably have a higher bioavailability of THC through the sublingual delivery mode than Sample No. 1.

With reference to Sample Nos. 3-12, the water solubility of THC continues to increase with the increasing HBC content. For example, in Sample No. 7, the concentration of HBC is increased to about 12.5 g/100 ml. As a result, about 13.10 mg/ml of THC is measured in the filtered emulsion, about 26.2% of THC is passed through the 0.45 μm filter (e.g., 13.10 mg/50 mg×100%=26.2%), and the THC water solubility is enhanced by about 751% (e.g., (13.10 mg-1.54 mg)/1.54 mg×100%=751%. In Sample No. 12, the concentration of HBC is increased to about 25 g/100 ml. As a result, about 24.5 mg/ml of THC is measured in the filtered emulsion, about 49.0% of THC passed through the 0.45 μm filter (e.g., 24.5 mg/50 mg×100%=49.0%), and the THC water solubility is enhanced by about 1490% (e.g., (24.5 mg-1.54 mg)/1.54 mg×100%=1490%).

With reference to Sample Nos. 13-16, in addition to HBC, the emulsions also include HPMC as a water solubility enhancing excipient. Sample No. 13 includes about 12.5 g/100 ml HBC, which is the same amount as in Sample 7, and Sample 13 further includes about 0.25 g/100 ml HPMC. As a result, the amount of THC measured in the filtered emulsion increases from about 13.10 mg/ml in Sample No. 7 to about 18.15 mg/ml in Sample No. 13. The fraction of THC passed through the 0.45 μm filter increases from about 26.20% in Sample No. 7 to about 36.30% in Sample No. 13. The THC water solubility is enhanced from about 751% in Sample No. 7 to about 1079% in Sample No. 13.

The presence of HPMC in addition to HBC appears to further enhance the water solubility of THC. For example, with reference to Sample Nos. 14-16, the concentration of HBC is maintained at about 12.5 g/100 ml, while the concentration of HPMC is furthered increased to about 0.50 g/100 ml in Sample No. 14, about 1.00 g/100 ml in Sample No. 15, and about 1.25 g/100 ml in Sample No. 16. The THC water solubility tends to increase with the increasing HPMC concentrations. For example, in Sample No. 16, the concentration of HBC is about 12.5 g/100 ml and the concentration of HPMC is about 1.25 g/100 ml. As a result, about 26.02 mg/ml of THC is measured in the filtered emulsion, about 52.04% of THC passed through the 0.45 μm filter (e.g., 26.02 mg/50 mg×100%=52.04%), and the THC water solubility is enhanced by about 1590% (e.g., (26.02 mg-1.54 mg)/1.54 mg×100%=1590%). This indicates that the water solubility of THC may be further enhanced by the presence of HPMC such that significantly more THC is dissolved in water to pass through the filter mimicking the sublingual tissue in the mouth, resulting in the higher THC bioavailability.

In these experiments, when the HBC content is increased to more than about 12.5 g/100 ml, the solution did not form a well-mixed homogenous emulsion. In particular, the compositions of Sample Nos. 8-12 did not form a well-mixed homogenous water emulsion. By adjusting the compositions (e.g., contents and concentrations of film-forming agent, plasticizer, solubilizing agent, buffer agent, surfactant, complexing agent, crystallization inhibitor, etc.), a homogenous emulsion may still form at HBC concentrations greater 12.5 g/100 ml and/or HPMC concentrations greater than 1.25 g/100 ml.

Example 2—CBD

TABLE 2

| | | | CBD | | |
|---|---|---|---|---|---|
| | CBD | HBC | | CBD content after filtration | |
| Sample No. | content (mg/ml) | (g/ 100 ml) | HPMC (g/100) | (mg/ml) | (%) | Enhancement (%) |
| 1 | 50 | 0 | 0 | 1.53 | 3.06% | 0 |
| 2 | 50 | 1 | 0 | 4.35 | 8.70% | 184 |
| 3 | 50 | 2.5 | 0 | 5.7 | 11.40% | 273 |
| 4 | 50 | 5 | 0 | 6.82 | 13.64% | 346 |
| 5 | 50 | 7.5 | 0 | 8.06 | 16.12% | 427 |
| 6 | 50 | 10 | 0 | 10.55 | 21.10% | 590 |
| 7 | 50 | 12.5 | 0 | 12.6 | 25.20% | 724 |

TABLE 2-continued

| | CBD | | | | | |
|---|---|---|---|---|---|---|
| | CBD | HBC | | CBD content after filtration | | |
| Sample No. | content (mg/ml) | (g/100 ml) | HPMC (g/100) | (mg/ml) | (%) | Enhancement (%) |
| 8 | 50 | 15 | 0 | 13.5 | 27.00% | 782 |
| 9 | 50 | 17.5 | 0 | 15.7 | 31.40% | 926 |
| 10 | 50 | 20 | 0 | 19.1 | 38.20% | 1148 |
| 11 | 50 | 22.5 | 0 | 20.79 | 41.58% | 1259 |
| 12 | 50 | 25 | 0 | 22.54 | 45.08% | 1373 |
| 13 | 50 | 12.5 | 0.25 | 16.43 | 32.86% | 974 |
| 14 | 50 | 12.5 | 0.5 | 21.6 | 43.20% | 1312 |
| 15 | 50 | 12.5 | 1 | 22.58 | 45.16% | 1376 |
| 16 | 50 | 12.5 | 1.25 | 24.63 | 49.26% | 1510 |

Example 3—THC-V

TABLE 3

| | THC-V | | | | | |
|---|---|---|---|---|---|---|
| | THC-V | | | THC-V content after filtration | | |
| Sample No. | Content (mg/ml) | HBC (g/100) | HPMC (g/100) | (mg/ml) | (%) | Enhancement (%) |
| 1 | 50 | 0 | 0 | 1.57 | 3.14% | 0 |
| 2 | 50 | 1 | 0 | 3.64 | 7.28% | 132 |
| 3 | 50 | 2.5 | 0 | 4.23 | 8.46% | 169 |
| 4 | 50 | 5 | 0 | 8.68 | 17.36% | 453 |
| 5 | 50 | 7.5 | 0 | 8.97 | 17.94% | 471 |
| 6 | 50 | 10 | 0 | 9.25 | 18.50% | 489 |
| 7 | 50 | 12.5 | 0 | 11.55 | 23.10% | 636 |
| 8 | 50 | 15 | 0 | 13.28 | 26.56% | 746 |
| 9 | 50 | 17.5 | 0 | 14.82 | 29.64% | 844 |
| 10 | 50 | 20 | 0 | 16.27 | 32.54% | 936 |
| 11 | 50 | 22.5 | 0 | 17.19 | 34.38% | 995 |
| 12 | 50 | 25 | 0 | 18.38 | 36.76% | 1071 |
| 13 | 50 | 12.5 | 0.25 | 13.85 | 27.70% | 782 |
| 14 | 50 | 12.5 | 0.5 | 16.43 | 32.86% | 946 |
| 15 | 50 | 12.5 | 1 | 18.92 | 37.84% | 1105 |
| 16 | 50 | 12.5 | 1.25 | 21.67 | 43.34% | 1280 |

Example 4—CBG

TABLE 4

| | CBG | | | | | |
|---|---|---|---|---|---|---|
| | CBG | | | CBG content after filtration | | |
| Sample No. | Content (mg/ml) | HBC (g/100) | HPMC (g/100) | (mg/ml) | (%) | Enhancement (%) |
| 1 | 50 | 0 | 0 | 1.5 | 3.00% | 0 |
| 2 | 50 | 1 | 0 | 4.35 | 8.70% | 190 |
| 3 | 50 | 2.5 | 0 | 5.29 | 10.58% | 253 |
| 4 | 50 | 5 | 0 | 6.45 | 12.90% | 330 |
| 5 | 50 | 7.5 | 0 | 9.42 | 18.84% | 528 |
| 6 | 50 | 10 | 0 | 12.24 | 24.48% | 716 |
| 7 | 50 | 12.5 | 0 | 12.96 | 25.92% | 764 |
| 8 | 50 | 15 | 0 | 14.22 | 28.44% | 848 |
| 9 | 50 | 17.5 | 0 | 16.45 | 32.90% | 997 |
| 10 | 50 | 20 | 0 | 20.38 | 40.76% | 1259 |
| 11 | 50 | 22.5 | 0 | 21.82 | 43.64% | 1355 |
| 12 | 50 | 25 | 0 | 23.96 | 47.92% | 1497 |
| 13 | 50 | 12.5 | 0.25 | 17.93 | 35.86% | 1095 |

TABLE 4-continued

| | CBG | | | | | |
|---|---|---|---|---|---|---|
| | CBG | | | CBG content after filtration | | |
| Sample No. | Content (mg/ml) | HBC (g/100) | HPMC (g/100) | (mg/ml) | (%) | Enhancement (%) |
| 14 | 50 | 12.5 | 0.5 | 24.65 | 49.30% | 1543 |
| 15 | 50 | 12.5 | 1 | 25.06 | 50.12% | 1571 |
| 16 | 50 | 12.5 | 1.25 | 25.77 | 51.54% | 1618 |

Example 5—CBN

TABLE 5

| | CBN | | | | | |
|---|---|---|---|---|---|---|
| | CBN | | | CBN content after filtration | | |
| Sample No. | Content (mg/ml) | HBC (g/100) | HPMC (g/100) | (mg/ml) | (%) | Enhancement (%) |
| 1 | 50 | 0 | 0 | 1.21 | 2.42% | 0 |
| 2 | 50 | 1 | 0 | 3.8 | 7.60% | 214 |
| 3 | 50 | 2.5 | 0 | 4.53 | 9.06% | 274 |
| 4 | 50 | 5 | 0 | 5.45 | 10.90% | 350 |
| 5 | 50 | 7.5 | 0 | 7.12 | 14.24% | 488 |
| 6 | 50 | 10 | 0 | 9.77 | 19.54% | 707 |
| 7 | 50 | 12.5 | 0 | 11.79 | 23.58% | 874 |
| 8 | 50 | 15 | 0 | 12.9 | 25.80% | 966 |
| 9 | 50 | 17.5 | 0 | 15 | 30.00% | 1140 |
| 10 | 50 | 20 | 0 | 17.82 | 35.64% | 1373 |
| 11 | 50 | 22.5 | 0 | 19.5 | 39.00% | 1512 |
| 12 | 50 | 25 | 0 | 21.81 | 43.62% | 1702 |
| 13 | 50 | 12.5 | 0.25 | 14.15 | 28.30% | 1069 |
| 14 | 50 | 12.5 | 0.5 | 16.72 | 33.44% | 1282 |
| 15 | 50 | 12.5 | 1 | 18.39 | 36.78% | 1420 |
| 16 | 50 | 12.5 | 1.25 | 20.04 | 40.08% | 1556 |

The present disclosure is not limited in terms of the particular aspects described in this application, which are intended as illustrations of various aspects only. Many modifications and variations can be made without departing from the scope of the invention, as will be apparent to those skilled in the art. Functionally equivalent methods within the scope of the disclosure, in addition to those enumerated herein, will be apparent to those skilled in the art from the following descriptions. Such modifications and variations are intended to fall within the scope of the appended claims. It is also to be understood that the terminology used herein is for the purpose of describing particular aspects only and is not intended to be limiting.

All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third. All language such as "up to," "at least," and the like includes the number recited and refers to ranges which can be subsequently broken down into subranges. Finally, a range includes each individual member. Thus, for example, a group having 1-3 cells refers to groups having 1, 2, or 3 cells.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed aspects.

The use of "a" or "an" is intended to include the singular and the plural, unless explicitly limited to the singular or the plural. For example, "a cannabinoid" may mean one cannabinoid or it may mean a plurality of cannabinoids. The use of "and" and "or" should be interpreted as "and/or," unless explicitly limited to the conjunctive or disjunctive. The terms "about" and "approximately" are intended to be equivalent, and each is intended to include the number modified, as well as +10% of the number modified. The terms "comprising" and "including" (and iterations of both) are intended to have the same meaning and are to be interpreted in the legally established open-ended manner. At each instance of the use of the terms "comprising" and "including" in the specification, it is contemplated that the phrase "consisting essentially of" or the term "consisting of" may be substituted therefor, along with the legally established legal meaning of the phrase or term.

What is claimed is:

1. An emulsion consisting essentially of:
   (1) water;
   (2) a *Cannabis sativa* strain;
   (3) a component selected from the group consisting of caproic acid, caprylic acid, capric acid, lauric acid, coconut oil, palm oil, olive oil, avocado oil, hemp seed oil, grape seed oil, glycerol, propylene glycol, oleic acid, linoleic acid, soybean oil, sunflower oil, peanut oil, corn oil, canola oil, rice bran oil, lard, suet, butter, and combinations thereof;
   (4) a component selected from the group consisting of polysorbate 20, polysorbate 40, polysorbate 60, polysorbate 80, span 80, polyoxyl 40 hydrogenated castor oil, macrogolglycerol hydroxystearate, polyglycerate 60, sorbitan stearate, sorbitans, stearic acid, polyoxyethylene (20) sorbitan monostearate, sorbitan monooleate, sorbitan oleate, polyethylene glycol, sodium bis(2-ethylhexyl) sulfosuccinate, sodium mono- and dimethylnaphthalene sulfonate, sunflower lecithin, sodium lauryl sulfate, poloxamers, quillaja extract, and combinations thereof;
   (5) a component selected from the group consisting of kleptose, cyclodextrin, β-cyclodextrin, 2-hydroxyproply-β-cyclodextrin, sulfobutylether β-cyclodextrin sodium salt, methylated β-cyclodextrin, glucosyl β-cyclodextrin, maltosyl β-cyclodextrin, and combinations thereof;
   (6) a component selected from the group consisting of polydextrose, pullulan, hydroxypropylmethylcellulose, hydroxypropyl cellulose, carboxymethyl cellulose, pectin, sodium alginate, xanthan gum, tragacanth gum, guar gum, acacia gum, arabic gum, gelatin, polyethylene oxide, polyvinylpyrrolidone, polyvinyl alcohol, polyethylene glycol, polyacrylic acid, methylmethacrylate copolymer, carboxyvinyl copolymers, ethyl cellulose, hydroxypropyl ethyl cellulose, cellulose acetate phthalate, hydroxypropyl methyl cellulose phthalate, methylcellulose, ethylcellulose, chitosan, chitin, agar, hydroxyethylcellulose, cellulose acetate phthalate, carboxymethyl ethylcellulose, hydroxypropylmethyl cellulose acetate succinate, polyvinyl acetate phthalate, maltodextrin, dextran, sodium carboxymethyl cellulose, poly(methacrylic acid-co-ethyl acrylate), poly(methacrylic acid-co-methyl methacrylate), poly(methacrylic acid-co-ethyl acrylate), poly(methacrylic acid-co-methyl methacrylate), polyvinylpyrrolidone, polylactic acid, poly-L-lactide, poly-D-lactide, poly(lactic-co-glycolic acid), and combinations thereof;
   (7) a component selected from the group consisting sucralose, menthol, mannitol, osmitrol, dextrose, sucrose, fructose, sodium chloride, potassium chloride, xylitol, sorbitol, lactose, potassium phosphate, acesulfame-K, advantame, alitame, aspartame, cyclamate, honey, maltodextrin, neohesperdine, dihydrochalcone, neotame, saccharin, thaumatin, brazzein, curculin, douxmatok, glycyrrhizin, levulose, maltose, miraculin, monatin, monellin, monk fruit, pentadin, *stevia*, stevioside, yacon syrup, agave syrup, barley malt, brown rice syrup, caramel, high maltose corn syrup, inverted sugar, isoglucose, tagatose, trehalose, D-tagatose, erythritol, glucitol, hydrogenated starch hydrolysate, isomalt, lacititol, maltitol, polydextrose, birch syrup, blackstrap molasses, coconut palm sugar, fructooligosaccharide, inulin, isomalto, oligosaccharide, maple syrup, molasses, oligofructose, rapadura, sorghum syrup, ginger, anise, cinnamon, peppermint, licorice, and combinations thereof; and
   (8) a component selected from the group consisting of cinnamon oil, wintergreen oil, peppermint oil, clove oil, bay oil, anise oil, *eucalyptus* oil, thyme oil, cedar leaf oil, nutmeg oil, sage oil, bitter almond oil, *cassia* oil, vanilla, lemon oil, orange oil, grape oil, lime oil, grapefruit oil, apple oil, pear oil, peach oil, strawberry oil, raspberry oil, cherry oil, plum oil, pineapple oil, apricot oil, mango, mint, chocolate, marshmallow, bubble gum, peanut butter, ginger, licorice, chicken flavor, beef flavor, fish flavor, pyridoxine, cobalamin, and combinations thereof.

2. The emulsion of claim 1, wherein the emulsion is at least partially contained within mucosally dissolvable film.

* * * * *